US00PP14170P29

(12) United States Plant Patent
Kientzler

(10) Patent No.: US PP14,170 P2
(45) Date of Patent: Sep. 23, 2003

(54) NEW GUINEA IMPATIENS PLANT NAMED 'KICABO'

(75) Inventor: Ludwig Kientzler, Gensingen (DE)

(73) Assignee: Innovaplant GmbH + Co. KG, Gensingen (DE)

( * ) Notice: Subject to any disclaimer, the term of this patent is extended or adjusted under 35 U.S.C. 154(b) by 0 days.

(21) Appl. No.: 10/200,297

(22) Filed: Jul. 22, 2002

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Kicabo', characterized by its rounded, upright and compact plant habit; freely branching growth habit; small dark green-colored foliage; freely flowering habit with flowers positioned above or beyond the foliage; and small white-colored flowers.

1 Drawing Sheet

Botancial classification/cultivar designation: *Impatiens hawkeri* cultivar Kicabo.

BACKGROUND OF THE INVENTION

The present Invention relates to a new and distinct cultivar of New Guinea Impatiens plant, botanically known as *Impatiens hawkeri,* and hereinafter referred to by the cultivar name Kicabo.

The new Impatiens is a product of a planned breeding program Inventor in Gensingen, Germany. The objective of the breeding program is to develop new compact Impatiens cultivars with interesting and unique flower and foliage colors.

The new Impatiens originated from a cross-pollination made by the Inventor of a proprietary *Impatiens hawkeri* selection identified as code number W90, not patented, as the female, or seed parent, with a proprietary *Impatiens hawkeri* selection identified as W662, not patented, as the male, or pollen parent. The cultivar Kicabo was discovered and selected by the Inventor as a flowering plant within the progeny of the stated cross-pollination in a controlled environment in Gensingen, Germany in April, 1998.

Asexual reproduction of the new cultivar by terminal cuttings taken at Gensingen, Germany, since the summer of 1998, has shown that the unique features of this new Impatiens are stable and reproduced true to type in successive generations.

SUMMARY OF THE INVENTION

The following traits have been repeatedly observed and are determined to be the unique characteristics of 'Kicabo'. These characteristics in combination distinguish 'Kicabo' as a new and distinct Impatiens cultivar:

1. Rounded, upright and compact plant habit.
2. Freely branching growth habit; bushy appearance.
3. Small dark green-colored foliage.
4. Freely flowering habit with flowers held above and beyond the foliage.
5. Small white-colored flowers.

Plants of the new Impatiens differ from plants of the parent selections primarily in flower color and plant growth habit.

Plants of the new Impatiens can be compared to plants of the cultivar Moorea, disclosed in U.S. Plant Pat. No. 9,147. In side-by-side comparisons conducted in Gensingen, Germany, plants of the new Impatiens differed from plants of the cultivar Moorea in the following characteristics:

1. Plants of the new Impatiens were more compact than plants of the cultivar Moorea.
2. Plants of the new Impatiens had smaller flowers than plants of the cultivar Moorea.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Impatiens.

The photograph at the top of the sheet comprises a side perspective view of a typical flowering plant of 'Kicabo' grown in a 10-cm container.

The photograph at the bottom of the sheet comprises a close-up view of a typical flower and leaves of 'Kicabo'.

DETAILED BOTANICAL DESCRIPTION

The cultivar Kicabo has not been observed under all possible environmental conditions. The phenotype may vary somewhat with variations in environment such as temperature and light intensity, without, however, any variance in genotype. The aforementioned photographs and the following observations and measurements describe plants grown in Encinitas, Calif., during the late spring, under commercial practice in an outdoor nursery with day temperatures about 24° C., night temperatures about 18° C., and light levels about 4,000 foot-candles. Plants used in the photographs and following description were about 14 weeks old and grown in 10-cm containers with one plant per container.

In the following description, color references are made to The Royal Horticultural Society Colour Chart, 1995 Edition, except where general terms of ordinary dictionary significance are used.

Botanical classification: *Impatiens hawkeri* cultivar Kicabo.

Parentage:

*Female, or seed, parent.*—Proprietary *Impatiens hawkeri* selection identified as code number W90, not patented.

*Male, or pollen, parent.*—Proprietary *Impatiens hawkeri* selection identified as code number W662, not patented.

Propagation:

*Type cutting.*—Terminal cuttings.

*Time to initiate roots.*—About 10 days at 20° C.

*Time to produce a rooted cutting or liner.*—About 21 days at 20° C.

*Root description.*—Fine, fibrous, and freely branching.

Plant description:

*General appearance.*—Rounded and somewhat upright; compact. Appropriate for 10-cm containers.

*Growth and branching habit.*—Freely branching with about four lateral branches developing at the base, dense and bushy growth. Pinching, that is, removal of the terminal apices, is typically not required. Moderately vigorous.

*Plant height.*—About 5 cm.

*Plant diameter.*—About 10 cm.

*Lateral branches.*—Length: About 2.5 cm. Diameter: About 3 mm. Internode length: About 1 cm. Texture: Smooth, glabrous. Color: 145B.

*Foliage description.*—Arrangement: Opposite or in whorls; simple. Length: About 5.5 cm. Width: About 2.8 cm. Shape: Elliptic. Apex: Acuminate. Base: Attenuate. Margin: Serrulate with ciliation. Texture, upper and lower surfaces: Smooth, glabrous.. Color: Young foliage, upper surface: 146A. Young foliage, lower surface: 146B. Fully expanded foliage, upper surface: 147A. Fully expanded foliage, lower surface: 147B. Venation, upper surface: 145D. Venation, lower surface: 147C to 147D. Petiole: Length: About 1.3 cm. Diameter: About 3 mm. Texture, upper and lower surfaces: Smooth, glabrous. Color, upper and lower surfaces: 145B.

Flower description:

*Flower type and flowering habit.*—Single axillary flowers. Freely flowering, usually about eight flowers and flower buds per lateral branch. Flowers positioned above and beyond the foliage and typically face upward or outward. Flowers flat to slightly cupped; rounded in shape. Flowers last about seven days on the plant. Petals self-cleaning; gynoecium persistent. Flowers not fragrant.

*Flowering season.*—Year-round under greenhouse conditions. In the garden, flowering from spring until fall.

*Flower height.*—About 3.7 cm.

*Flower width.*—About 4 cm.

*Flower depth.*—About 1 cm.

*Flower buds* (*at stage of showing color*).—Rate of opening: From showing color to fully open flower, typically about 2 to 3 days depending on temperature. Length: About 1.5 cm. Diameter: About 8 mm. Shape: Ovoid. Color: 157C to 157D.

*Petals.*—Quantity: Single, five per flower. Length: Banner petal: About 1.8 cm. Lateral petals: About 2.1 cm. Base petals: About 2.3 cm. Width: Banner petal: About 3.2 cm. Lateral petals: About 2.4 cm. Base petals: About 2.7 cm. Shape: Cordate. Apex: Emarginate. Base: Acute. Margin: Entire. Texture: Smooth; velvety. Color: When opening, upper surface: 155C. When opening, lower surface: 157D. Fully opened, upper and lower surfaces: 155D.

*Spur.*—Length: About 4.2 cm. Texture: Smooth, glabrous. Color: 145C.

*Peduncles.*—Length: About 3 cm. Diameter: About 1 mm. Strength: Strong. Angle: About 50 to 60° from vertical. Texture: Smooth, glabrous. Color: 145B.

*Reproductive organs.*—Androecium: Stamen number: Five fused at anthers, filaments free. Anther shape: Oblong. Anther size: About 3.5 mm by 6 mm. Anther color: 155A. Amount of pollen: Scarce to moderate. Pollen color: 155A. Gynoecium: Pistil length: About 4 mm. Stigma color: 145D. Style color: 144A. Ovary color: 144A.

*Seed/fruit.*—Seed and fruit development has not been observed.

Disease/pest resistance: Plants of the new Impatiens have not been observed to be resistant to pathogens and pests common to Impatiens.

Temperature tolerance: Plants of the new Impatiens have been observed to tolerate temperatures from 4 to 34° C.

It is claimed:

1. A new and distinct cultivar of New Guinea Impatiens plant named 'Kicabo', as illustrated and described.

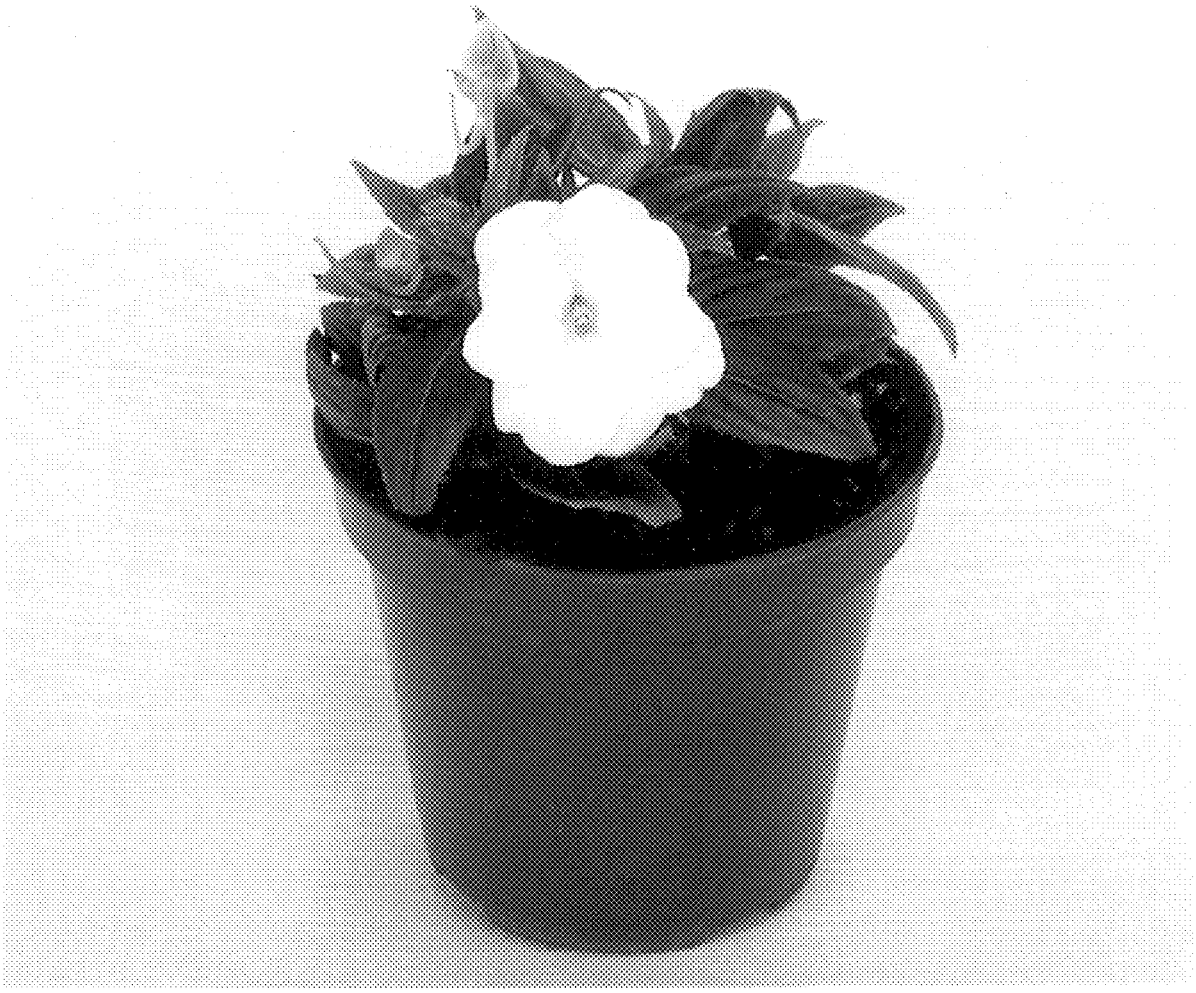
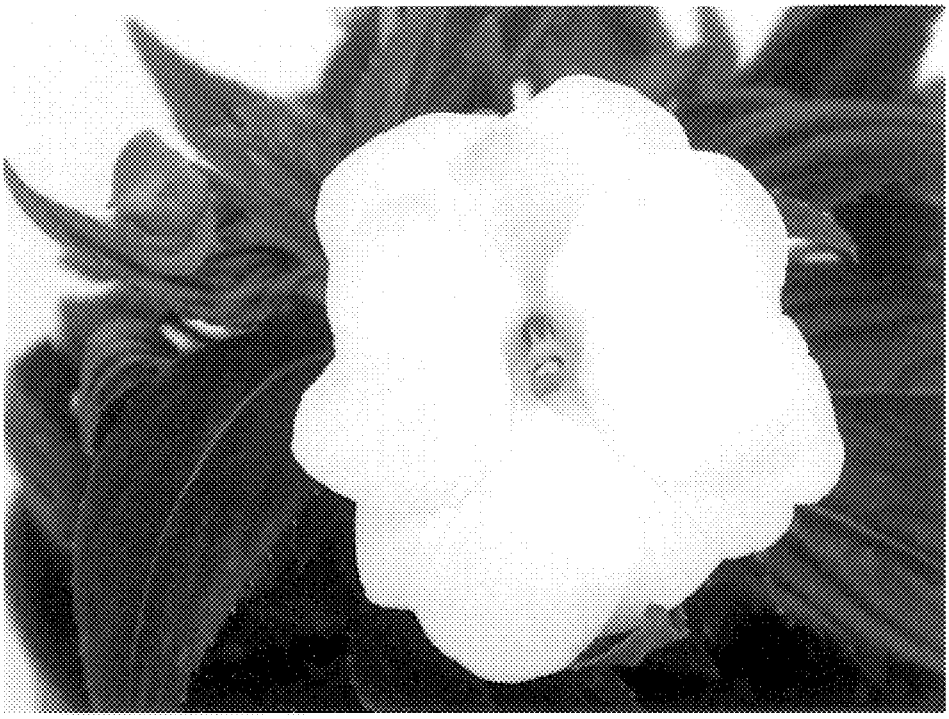

* * * * *